United States Patent
Takahashi

(10) Patent No.: US 8,717,427 B2
(45) Date of Patent: May 6, 2014

(54) ENDOSCOPE

(71) Applicant: Kazuhiko Takahashi, Hachioji (JP)

(72) Inventor: Kazuhiko Takahashi, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 4 days.

(21) Appl. No.: 13/748,185

(22) Filed: Jan. 23, 2013

(65) Prior Publication Data

US 2013/0201309 A1 Aug. 8, 2013

Related U.S. Application Data

(63) Continuation of application No. PCT/JP2012/063347, filed on May 24, 2012.

(30) Foreign Application Priority Data

Jul. 28, 2011 (JP) ................................. 2011-165246

(51) Int. Cl.
*A62B 1/04* (2006.01)
*A61B 1/00* (2006.01)

(52) U.S. Cl.
USPC .............................. 348/65; 600/146; 600/152

(58) Field of Classification Search
USPC ..................................... 600/146, 152; 348/65
See application file for complete search history.

(56) References Cited

U.S. PATENT DOCUMENTS

2003/0078475 A1* 4/2003 Hirata et al. .................. 600/152
2003/0092965 A1* 5/2003 Konomura et al. ........... 600/146

FOREIGN PATENT DOCUMENTS

| JP | A-59-225034 | 12/1984 |
| JP | A-63-267326 | 11/1988 |
| JP | A-6-68711 | 3/1994 |
| JP | A-07-140398 | 6/1995 |
| JP | A-09-010172 | 1/1997 |
| JP | A-2001-258819 | 9/2001 |
| JP | A-2004-8342 | 1/2004 |

OTHER PUBLICATIONS

Aug. 28, 2012 International Search Report issued in Application No. PCT/JP2012/063347 (with translation).

* cited by examiner

*Primary Examiner* — Sath V Perungavoor
*Assistant Examiner* — Xiaolan Xu
(74) *Attorney, Agent, or Firm* — Oliff PLC

(57) ABSTRACT

An endoscope includes a bending operation knob inputting a bending operation of a bending section in first perpendicular directions, a touch surface which is exposed in an outer surface of a grip casing and on which a bending operation of the bending section in second perpendicular directions is input, and a positional information calculator calculating a positional information of a touched region with time, the touched region being a region that is touched in the touch surface. The endoscope includes a positional change detector detecting a positional change of the touched region when the bending operation of the bending section in the second perpendicular directions is input, and a drive controller controlling a drive state of a drive member in accordance with the positional change of the touched region.

7 Claims, 8 Drawing Sheets

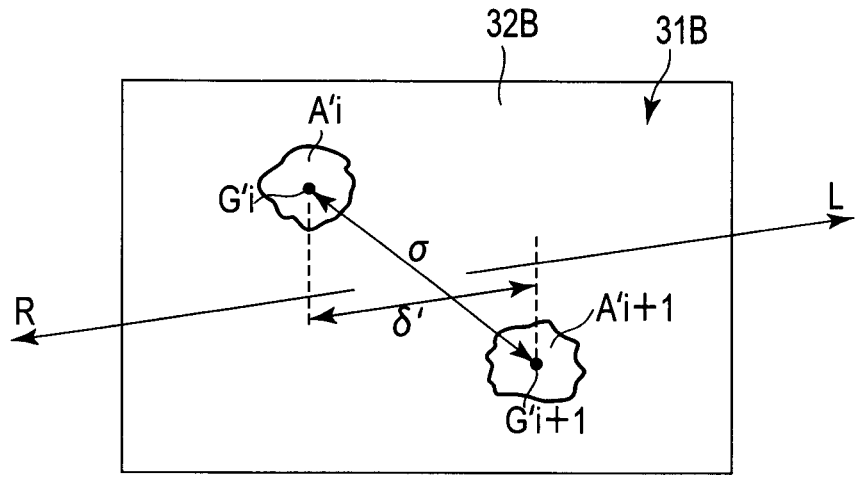
F I G. 9
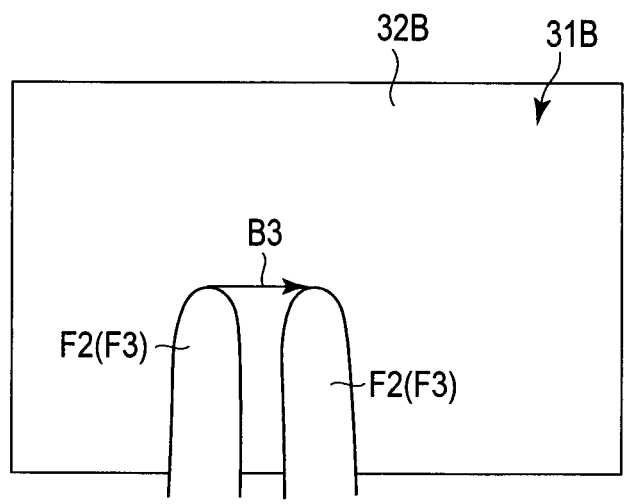
F I G. 10

ENDOSCOPE

CROSS-REFERENCE TO RELATED APPLICATIONS

This is a Continuation Application of PCT Application No. PCT/JP2012/063347, filed May 24, 2012 and based upon and claiming the benefit of priority from prior Japanese Patent Application No. 2011-165246, filed Jul. 28, 2011, the entire contents of which are incorporated herein by reference.

BACKGROUND OF THE INVENTION

1. Field of the Invention

The present invention relates to an endoscope including an insertion section provided with a bending section which is configured to bend in first perpendicular directions perpendicular to longitudinal directions and in second perpendicular directions perpendicular to the longitudinal directions and perpendicular to the first perpendicular directions.

2. Description of the Related Art

Jpn. UM Appln. KOKAI Publication No. 6-68711 has disclosed an endoscope including an insertion section provided with a bending section which configured to bend in first perpendicular directions perpendicular to longitudinal directions and in second perpendicular directions perpendicular to the longitudinal directions and perpendicular to the first perpendicular directions. Here, the first perpendicular directions are up-and-down directions (UD directions) of a subject image obtained by an imaging element, and the second perpendicular directions are left-and-right directions (LR directions) of the subject image. In this endoscope, a first bending operation knob configured to perform a bending operation in the first perpendicular directions and a second bending operation knob configured to perform a bending operation in the second perpendicular directions are provided on an outer surface of a grip casing of a grip section. The second bending operation knob is located to an outside of the first bending operation knob, and provided coaxially with the first bending operation knob.

BRIEF SUMMARY OF THE INVENTION

According to one aspect of the present invention, an endoscope includes that an insertion section including a bending section which is configured to bend in first perpendicular directions perpendicular to longitudinal directions and in second perpendicular directions perpendicular to the longitudinal directions and perpendicular to the first perpendicular directions; a grip section which includes a grip casing, and which is provided to a proximal direction side of the insertion section; a bending operation knob which is attached to the grip casing, and which is configured to input a bending operation of the bending section in the first perpendicular directions; a touch surface which is exposed in an outer surface of the grip casing, and on which a bending operation of the bending section in the second perpendicular directions is input; a positional information calculator which is configured to calculate a positional information of a touched region with time, the touched region being a region that is touched in an input of the bending operation in the second perpendicular directions on the touch surface; a positional change detector which is configured to detect, in accordance with the positional information of the touched region with the time, a positional change of the touched region when the bending operation of the bending section in the second perpendicular directions is input; a drive member which is configured to be driven to bend the bending section in the second perpendicular directions; and a drive controller which is configured to control a drive state of the drive member in accordance with the positional change of the touched region.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 9 is a schematic diagram showing a state in which a position of a touched region on a touch surface is changed by the bending operation in the second perpendicular directions in a slide pad according to a referential example;

FIG. 10 is a schematic diagram showing the bending operation of the bending section in the second perpendicular directions when the amount of bending of the bending section according to the referential example in the second perpendicular directions decreased.

DETAILED DESCRIPTION OF THE INVENTION

First Embodiment

A first embodiment of the present invention is described with reference to FIG. 1 to FIG. 11.

Figure 1:
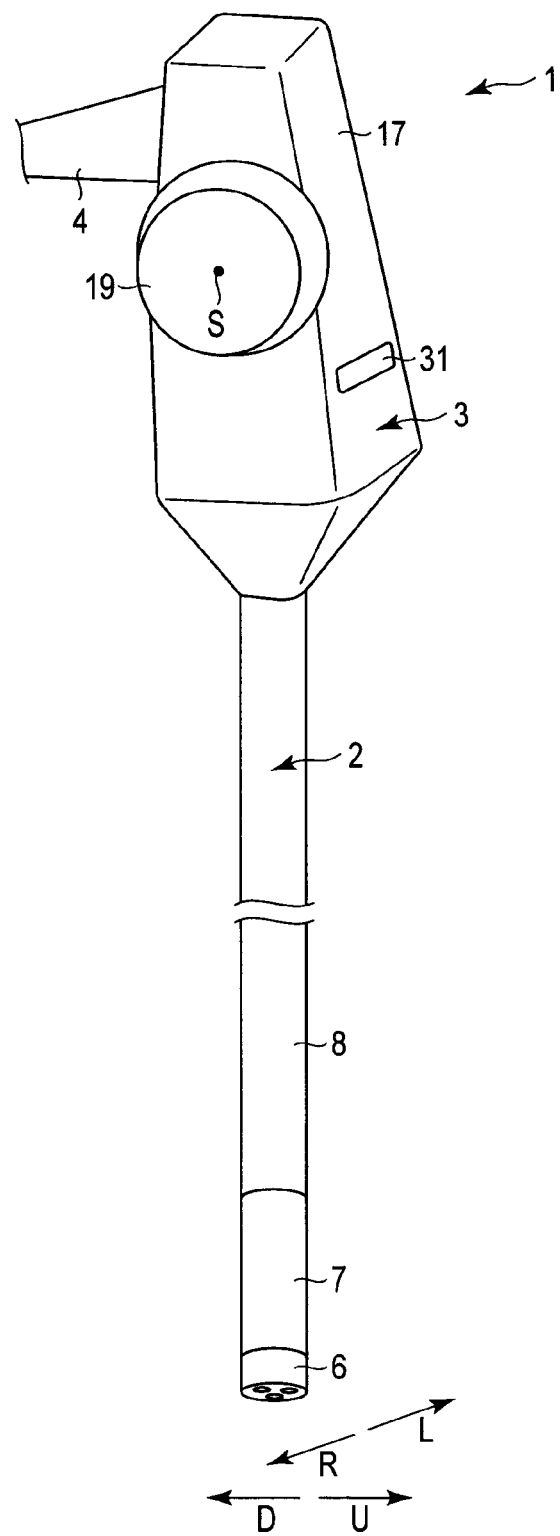
FIG. 1 is a schematic perspective view showing an endoscope according to a first embodiment of the present invention.
Figure 2:
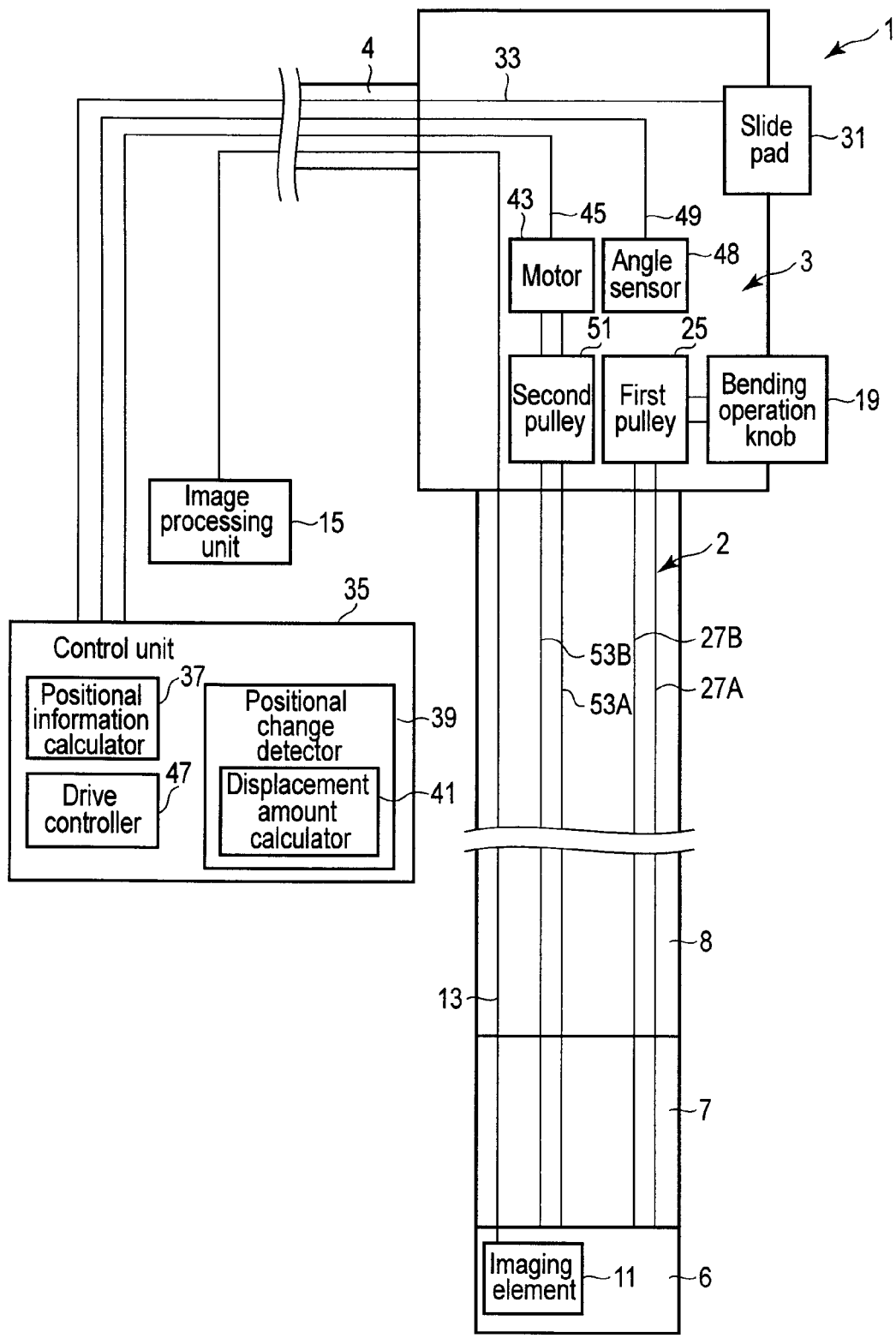
FIG. 2 is a block diagram showing the endoscope according to the first embodiment.

FIG. 1 and FIG. 2 are views showing an endoscope 1 according to the present embodiment. As shown in FIG. 1 and FIG. 2, the endoscope 1 includes an insertion section 2 which is configured to be inserted into a body cavity and which extends in longitudinal directions, and a grip section 3 provided to a proximal direction side of the insertion section 2. One end of a universal cord 4 is connected to the grip section 3. A scope connector (not shown) is provided at the other end of the universal cord 4.

The insertion portion 2 includes a distal rigid section 6, a bending section 7 provided to the proximal direction side of the distal rigid section 6, and a flexible tube section 8 provided to the proximal direction side of the bending section 7. The bending section 7 is configured to bend in first perpendicular directions (a direction of arrow U and a direction of arrow D in FIG. 1) perpendicular to the longitudinal directions, and in second perpendicular directions (a direction of arrow L and a direction of arrow R in FIG. 1) perpendicular to the longitudinal directions and perpendicular to the first perpendicular directions.

An imaging element 11 such as a CCD is provided in a distal end portion of the insertion section 2. A distal end of an electrical signal line 13 is connected to the imaging element 11. A proximal end of the electrical signal line 13 is connected to an image processing unit 15 such as an image processor via the scope connector through an inside of the insertion section 2, an inside of the grip section 3, and an inside of the universal cord 4. A light guide (not shown) configured to guide light to illuminate a subject extends from the distal end portion of the insertion section 2 through the inside of the insertion section 2 along the longitudinal directions. A proximal end of the light guide is connected to a light source unit (not shown) via the scope connector through the inside of the grip section 3 and the inside of the universal cord 4. Here, the first perpendicular directions correspond to up-and-down directions (UD directions) of a subject image obtained (pictured) by the imaging element 11. The second perpendicular directions correspond to left-and-right directions (LR directions) of the subject image.

The grip section 3 includes a grip casing 17 which is an exterior. A bending operation knob 19 is attached to the grip casing 17. A bending operation of the bending section 7 in the first perpendicular directions is performed (input) by a rotation of the bending operation knob 19. The space between the bending operation knob 19 and the grip casing 17 is kept watertight.

Figure 3:
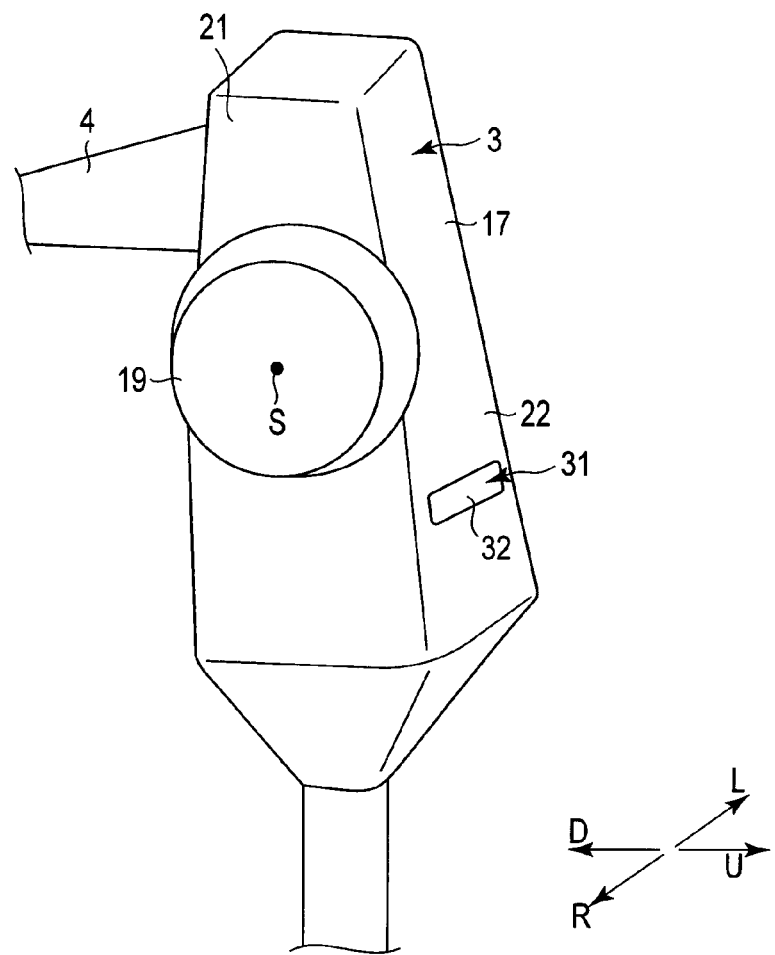
FIG. 3 is a schematic perspective view showing the configuration of a grip section of the endoscope according to the first embodiment.

FIG. 3 is a view showing the configuration of the grip section 3. As shown in FIG. 1 and FIG. 3, the grip casing 17 includes a first outer surface portion 21 in which an outer surface faces toward one of the second perpendicular directions (the direction of arrow L and the direction of arrow R in FIG. 1 and FIG. 3), and a second outer surface portion 22 in which an outer surface faces toward one of the first perpendicular directions (the direction of arrow U and the direction of arrow D in FIG. 1 and FIG. 3). The bending operation knob 19 is provided on the first outer surface portion 21. The bending operation knob 19 is attached to the first outer surface portion 21 so that its rotation axis S is parallel to the second perpendicular directions. Thus, the bending operation knob 19 is rotated substantially parallel to the first perpendicular directions by the bending operation.

As shown in FIG. 2, a first pulley 25 is provided inside the grip casing 17. The first pulley 25 is rotated by the bending operation of the bending operation knob 19 in the first perpendicular directions. Proximal ends of two first bending wires 27A and 27B are connected to the first pulley 25. Distal ends of the first bending wires 27A and 27B are connected to a distal end portion of the bending section 7 through an inside of the flexible tube section 8. One of the first bending wires 27A and 27B is pulled by the rotation of the first pulley 25.

When the first bending wire 27A is pulled, the bending section 7 bends toward the direction of arrow U in FIG. 1. On the other hand, when the first bending wire 27B is pulled, the bending section 7 bends toward the direction of arrow D in FIG. 1. In this way, the bending section 7 bends in the first perpendicular directions.

As shown in FIG. 1 to FIG. 3, a slide pad 31 which is a touched region detector is provided to the grip casing 17. The bending operation of the bending section 7 in the second perpendicular directions is performed (input) by the slide pad 31. The slide pad 31 includes a touch surface 32 located on the second outer surface portion 22 of the outer surface of the grip casing 17. During the bending operation in the second perpendicular directions, the slide pad 31 detects, with time, a region of the touch surface 32 that has been touched as a touched region. In accordance with pressure or static electricity, the slide pad 31 detects, as a touched region, a region that has been touched by a surgeon.

As shown in FIG. 2, one end of an electrical signal line 33 is connected to the slide pad 31. The other end of the electrical signal line 33 is connected to a control unit 35 through the inside of the universal cord 4. The control unit 35 includes a positional information calculator 37 configured to calculate a positional information of the detected touched region with time. The positional information calculator 37 is configured to calculate a position of a center of gravity of the touched region as the positional information of the touched region.

The control unit 35 includes a positional change detector 39. In accordance with the positional information of the touched region with time, the positional change detector 39 is configured to detect a positional change of the touched region when the bending operation of the bending section 7 in the second perpendicular directions is performed (input). The positional change detector 39 includes a displacement amount calculator 41. The displacement amount calculator 41 will be described in detail later.

A motor 43 which is a drive member is provided inside the grip casing 17. The motor 43 is electrically connected to the control unit 35 via an electrical signal line 45. The control unit 35 includes a drive controller 47 configured to control a drive state of the motor 43. The drive controller 47 is configured to control the drive state of the motor 43 in accordance with the positional change of the touched region detected by the positional change detector 39.

An angle sensor 48 is provided inside the grip casing 17. The angle sensor 48 is electrically connected to the control unit 35 via an electrical signal line 49. The angle sensor 48 is configured to detect a rotation angle of the motor 43. The drive controller 47 is configured to control the drive state of the motor 43 in accordance with the detected rotation angle of the motor 43.

As shown in FIG. 2, a second pulley 51 is provided inside the grip casing 17. The second pulley 51 is rotated when the motor 43 is driven by the bending operation in the second perpendicular directions in the slide pad 31. Proximal ends of two second bending wires 53A and 53B are connected to the second pulley 51. Distal ends of the second bending wires 53A and 53B are connected to the distal end portion of the bending section 7 through the inside of the flexible tube section 8. One of the second bending wires 53A and 53B is pulled by the rotation of the second pulley 51. When the second bending wire 53A is pulled, the bending section 7 bends toward the direction of arrow L in FIG. 1. On the other hand, when the second bending wire 53B is pulled, the bending section 7 bends toward the direction of arrow R in FIG. 1. In this way, the bending section 7 bends in the second perpendicular directions when the motor 43 is driven.

Figure 4:
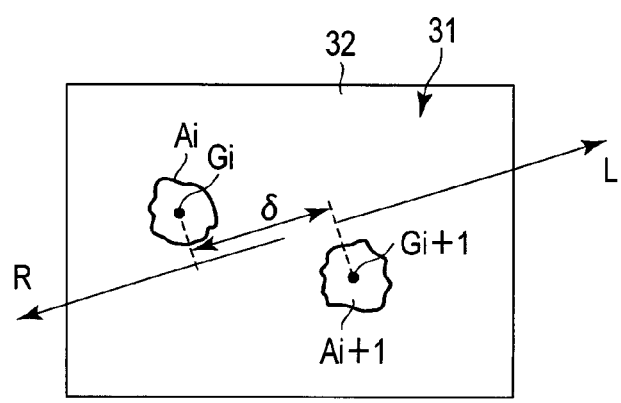
FIG. 4 is a schematic diagram illustrating processing in a displacement amount calculator in the endoscope according to the first embodiment.

FIG. 4 is a diagram illustrating processing in the displacement amount calculator 41. As shown in FIG. 4, a touched region Ai is detected by the slide pad 31 at a time ti. At the same time, the center of gravity Gi of the touched region Ai is calculated by the positional information calculator 37 as positional information of the touched region Ai. The position of the touched region is changed by the bending operation of the bending section 7 in the second perpendicular directions. A touched region Ai+1 is detected by the slide pad 31 at a time ti+1. At the same time, the center of gravity Gi+1 of the touched region Ai+1 is calculated by the positional information calculator 37 as positional information of the touched region Ai+1. As described above, the position of the touched region is changed from the center of gravity Gi to the center of gravity Gi+1 by the bending operation of the bending section 7 in the second perpendicular directions.

The displacement amount calculator 41 calculates a displacement amount of the touched region in the second perpendicular directions (the direction of arrow L and the direction of arrow R in FIG. 4) which are reference directions in the positional change of the touched region. A displacement amount δ in the second perpendicular directions between the center of gravity Gi and the center of gravity Gi+1 is calculated. The drive controller 47 controls the drive state of the motor 43 in accordance with the calculated displacement amount δ of the touched region in the second perpendicular directions. Therefore, the bending portion 7 performs a bending motion in the second perpendicular directions in accordance with the calculated displacement amount δ of the touched region in the second perpendicular directions.

Although the drive state of the motor 43 is controlled in accordance with the displacement amount δ of the touched region in the second perpendicular directions in the present embodiment, the present invention is not limited thereto. The displacement amount calculator 41 has only to calculate a displacement amount of the touched region in the reference directions parallel to the outer surface of the grip casing 17 during the positional change of the touched region. Further, the drive controller 47 has only to control the drive state of the motor 43 in accordance with the displacement amount of the touched region in the reference directions.

Figure 5:
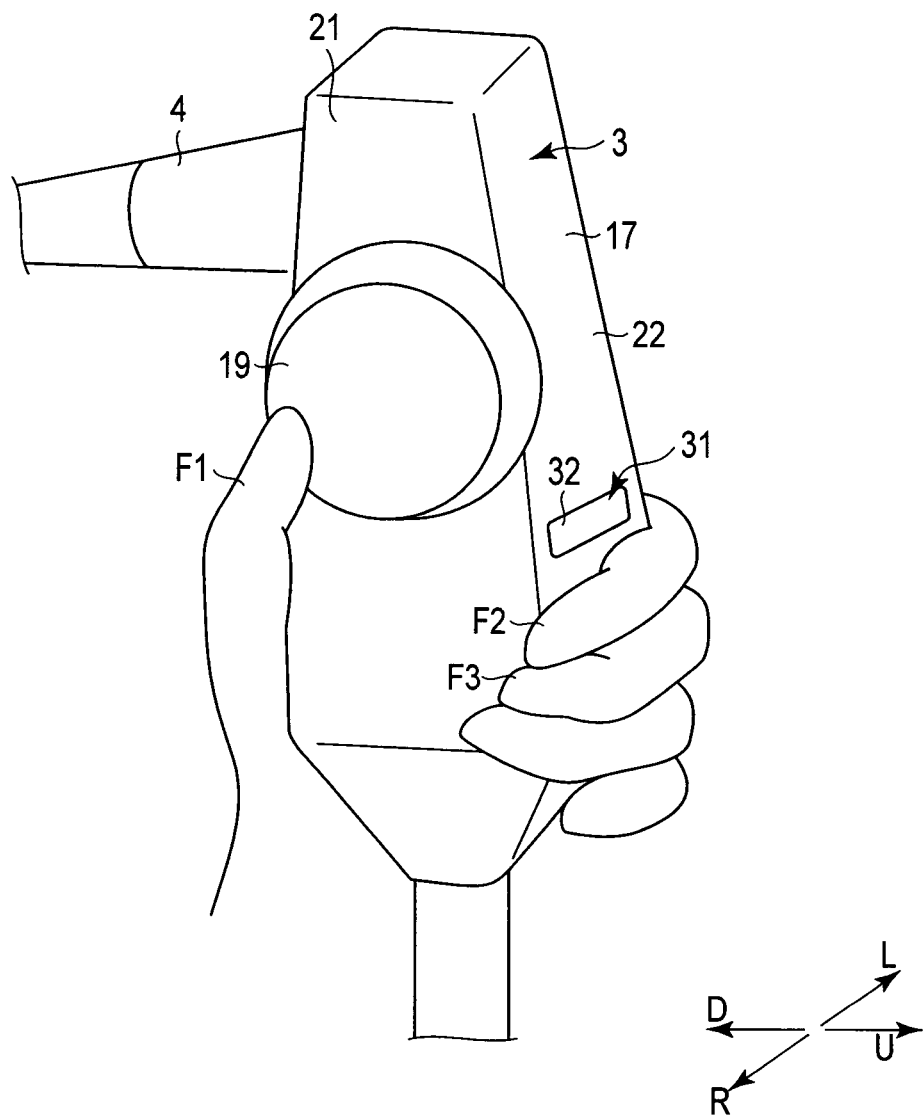
FIG. 5 is a schematic perspective view showing a state in which a surgeon grips a grip casing of the endoscope according to the first embodiment with one hand.

Now, the functions of the endoscope 1 are described. FIG. 5 is a view showing a state in which the surgeon grips the grip casing 17 with one of two hands. As shown in FIG. 5, when the surgeon grips the grip casing 17 with one hand, the bending operation knob 19 is rotated with a thumb F1 to perform (input) the bending operation of the bending section 7 in the first perpendicular directions. A forefinger F2 or a middle finger F3 is moved on the touch surface 32 of the slide pad 31 to perform (input) the bending operation of the bending section 7 in the second perpendicular directions.

Figure 6:
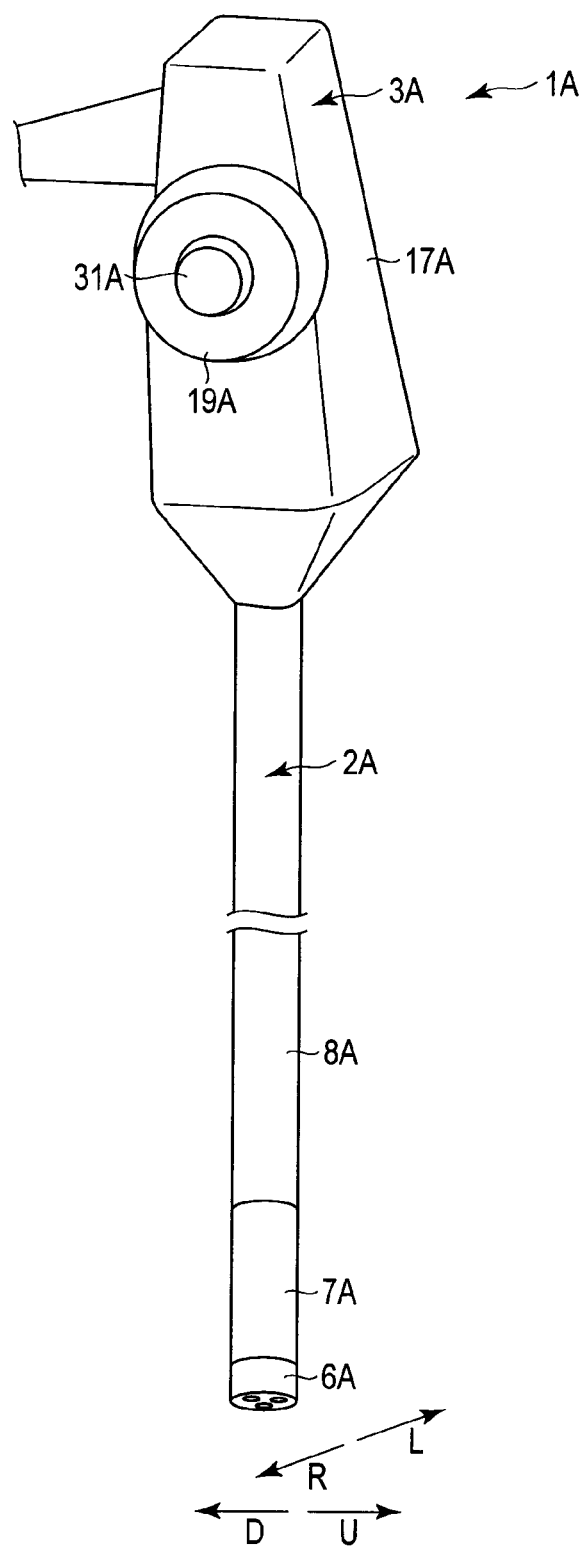
FIG. 6 is a schematic perspective view showing an endoscope according a first comparative example.

Here, suppose an endoscope 1A shown in FIG. 6 as a first comparative example. In the endoscope 1A, a bending operation of a bending section 7A in the first perpendicular directions (the direction of arrow U and the direction of arrow D in FIG. 6) is performed by a first bending operation knob 19A, and a bending operation of the bending section 7A in the second perpendicular directions (the direction of arrow L and the direction of arrow R in FIG. 6) is performed by a second bending operation knob 31A. In the endoscope 1A, the second bending operation knob 31A is located to an outside of the first bending operation knob 19A, and provided coaxially with the first bending operation knob 19A. Therefore, when the surgeon perform both the bending operation in the first perpendicular direction and the bending operation in the second perpendicular direction with one of two hands, the finger of the surgeon does not easily reach the second bending operation knob 31A. As the first bending operation knob 19A and the second bending operation knob 31A are coaxial, directions in which the first bending operation knob 19A is rotated by the bending operation is the same as directions in which the second bending operation knob 31A is rotated by the bending operation. As the directions in which the first bending operation knob 19A is rotated by the bending operation in the first perpendicular directions is the same as the directions in which the second bending operation knob 31A is rotated by the bending operation in the second perpendicular directions perpendicular to the first perpendicular directions, the surgeon cannot easily perform the bending operation of the bending section 7A in the second perpendicular directions.

In contrast, in the endoscope 1 according to the present embodiment, the bending operation knob 19 is attached to the first outer surface portion 21 in which the outer surface of the grip casing 17 faces toward one of the second perpendicular directions, and the touch surface 32 of the slide pad 31, which is the touched region detector, is located to the second outer surface portion 22 in which the outer surface of the grip casing 17 faces toward one of the first perpendicular directions. Therefore, when the surgeon grips the grip casing 17 with one hand, the bending operation knob 19 is easily rotated with the thumb F1, and the bending operation of the bending section 7 in the first perpendicular directions is easily performed (input). Moreover, the forefinger F2 or the middle finger F3 is easily moved on the touch surface 32 of the slide pad 31, and the bending operation of the bending section 7 in the second perpendicular directions is easily performed (input).

In the endoscope 1, the bending operation knob 19 is attached to the first outer surface portion 21 so that its rotation axis S is parallel to the second perpendicular directions. Thus, the bending operation knob 19 is rotated substantially parallel to the first perpendicular directions by the bending operation. As the rotation directions of the bending operation knob 19 are substantially parallel to the first perpendicular directions in which the bending portion 7 is bent by the bending operation, the surgeon more easily perform (input) the bending operation of the bending section 7 in the first perpendicular directions.

In the endoscope 1, the displacement amount calculator 41 calculates the displacement amount δ of the touched region in the second perpendicular directions which are the reference directions in the positional change of the touched region on the touch surface 32. The drive state of the motor 43 is controlled in accordance with the displacement amount δ of the touched region in the second perpendicular directions. That is, the bending portion 7 bends in the second perpendicular directions in accordance with the displacement amount δ of the touched region in the second perpendicular directions in the bending operation. When the surgeon grips the grip casing 17 with one hand, the forefinger F2 or the middle finger F3 is easily moved on the touch surface 32 of the slide pad 31. Therefore, the bending operation of the bending section 7 in the second perpendicular directions is more easily performed (input). Moreover, in the endoscope 1 according to the present embodiment, the second perpendicular directions in which the bending portion 7 is bent by the bending operation are the reference directions of the displacement amount δ, so that the surgeon more easily perform the bending operation of the bending section 7 in the second perpendicular directions.

Figure 7:
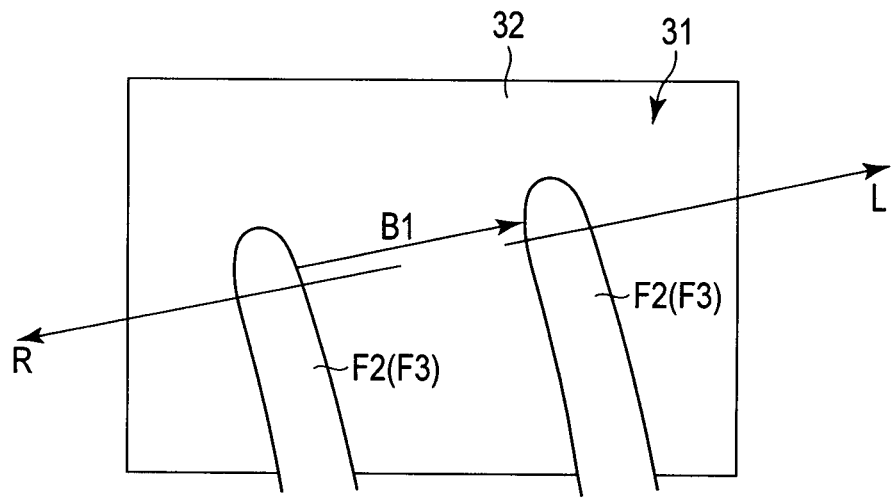
FIG. 7 is a schematic diagram showing the bending operation of a bending section in second perpendicular directions when an amount (degree) of bending of the bending section of the endoscope according to the first embodiment in the second perpendicular directions is increased.
Figure 8:
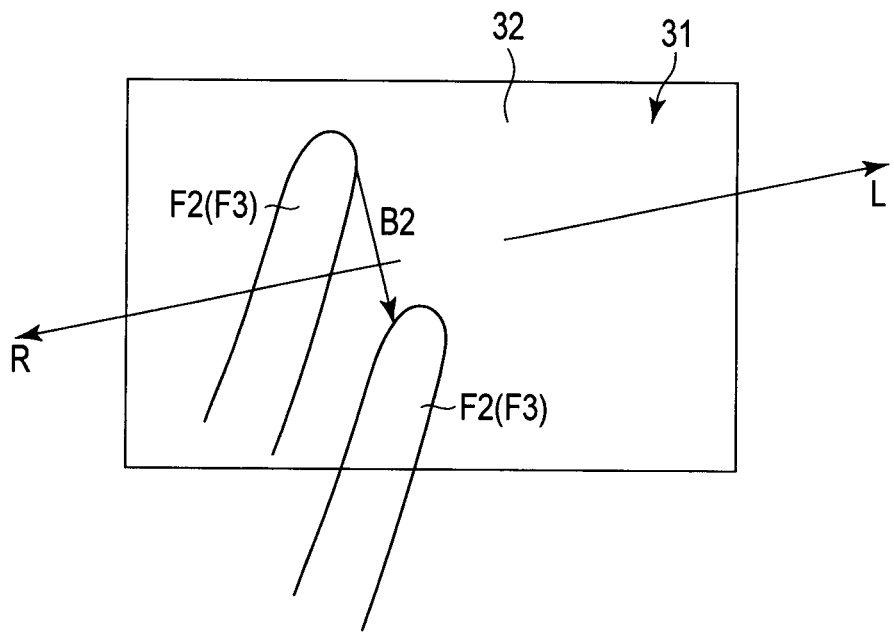
FIG. 8 is a schematic diagram showing the bending operation of the bending section in the second perpendicular directions when the amount (degree) of bending of the bending section of the endoscope according to the first embodiment in the second perpendicular directions is decreased.

FIG. 7 and FIG. 8 are diagrams illustrating the bending operation of the bending section 7 in the second perpendicular directions. As shown in FIG. 7, in order to increase the amount (degree) of bending of the bending section 7 in the second perpendicular directions, the forefinger F2 or the middle finger F3 is moved (arrow B1 in FIG. 7) on the touch surface 32 to increase the displacement amount in the second perpendicular directions (the direction of arrow L and the direction of arrow R in FIG. 7 and FIG. 8). That is, the forefinger F2 or the middle finger F3 is moved on the touch surface 32 substantially parallel to the second perpendicular directions which are the reference directions. On the other hand, as shown in FIG. 8, in order to decrease the amount (degree) of bending of the bending section 7 in the second perpendicular directions, the forefinger F2 or the middle finger F3 is moved (arrow B2 in FIG. 8) on the touch surface 32 to decrease the displacement amount in the second perpendicular directions. That is, the forefinger F2 or the middle finger F3 is moved on the touch surface 32 to deviate from the second perpendicular directions which are the reference directions.

Here, suppose a slide pad 31B shown in FIG. 9 and FIG. 10 as a referential example. As shown in FIG. 9, in this referential example, the drive state of a motor 43B is controlled in accordance with an amount (degree) of movement during the positional change of the touched region. That is, when the position is changed from a touched region A'i to a touched region A'i+1 by the bending operation in the second perpendicular directions, an amount of movement σ from the center of gravity G'i to the center of gravity G'i+1 is calculated. The drive state of the motor 43B is controlled in accordance with the amount of movement σ, and a bending section 7B performs bending motion in the second perpendicular directions. Therefore, even if a displacement amount δ' of the touched region in the second perpendicular directions (the direction of arrow L and the direction of arrow R in FIG. 9) is small when the position of the touched region is changed on a touch surface 32B by the bending operation in the second perpendicular directions, the amount of bending of the bending section 7B in the second perpendicular directions is great when the amount of movement σ of the touched region is great. Thus, as shown in FIG. 10, the amount of movement of the forefinger F2 or the middle finger F3 on the touch surface 32B need to be decreased (arrow B3 in FIG. 10) to decrease the amount of bending of the bending section 7B in the second perpendicular directions. Therefore, when the amount of bending of the bending section 7B in the second perpendicular directions is small, the surgeon does not easily perform (input) the bending operation of the bending section 7B in the second perpendicular directions.

In contrast, according to the present embodiment, in order to decrease the amount (degree) of bending of the bending section 7 in the second perpendicular directions, the forefinger F2 or the middle finger F3 is moved (arrow B2 in FIG. 8) on the touch surface 32 to decrease the displacement amount in the second perpendicular directions. That is, the forefinger F2 or the middle finger F3 is moved on the touch surface 32 to deviate from the second perpendicular directions which are the reference directions. Thus, even when the amount of bending of the bending section 7 in the second perpendicular directions is decreased, the amount of movement of the forefinger F2 or the middle finger F3 does not need to be decreased as long as the displacement amount of the touched region in the second perpendicular directions is small. Therefore, even when the amount (degree) of bending of the bending section 7 in the second perpendicular directions is small, the surgeon easily performs (inputs) the bending operation of the bending section 7 in the second perpendicular directions.

Figure 11:
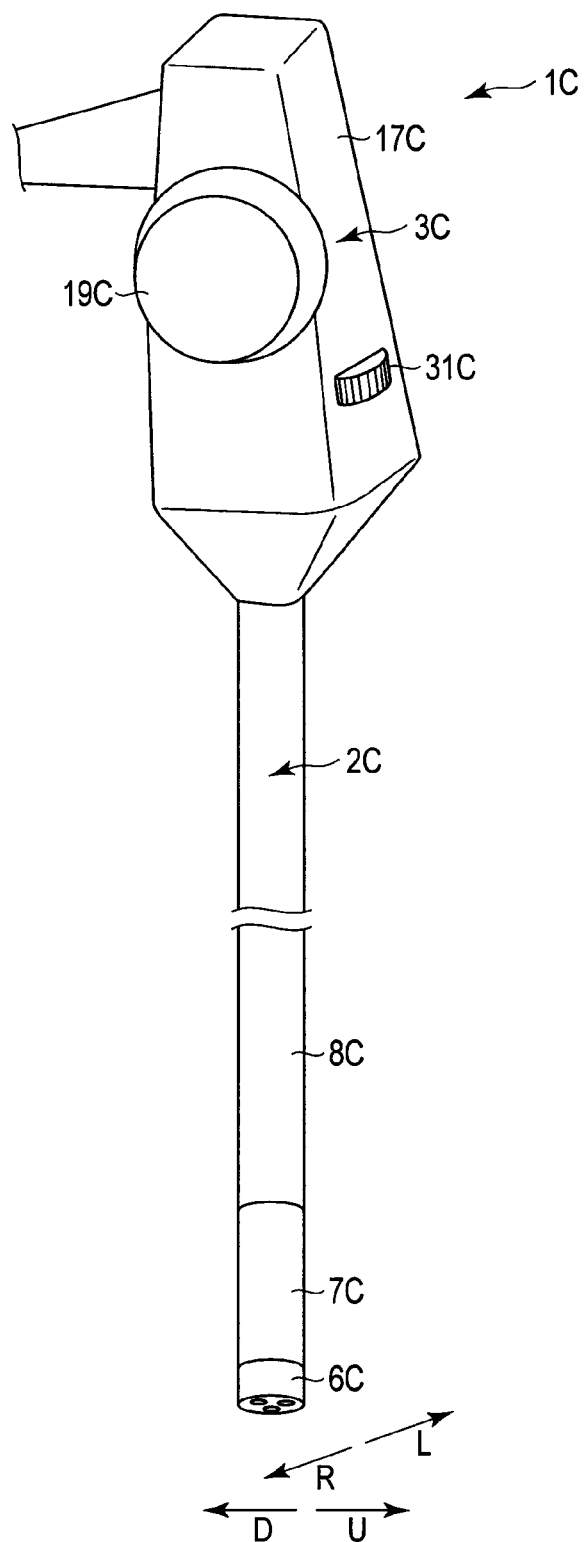
FIG. 11 is a schematic perspective view showing an endoscope according a second comparative example.

Suppose an endoscope 1C shown in FIG. 11 as a second comparative example. In the endoscope 1C, a bending operation of a bending section 7C in the first perpendicular directions (the direction of arrow U and the direction of arrow D in FIG. 11) is performed (input) by a first bending operation knob 19C, and a bending operation of the bending section 7C in the second perpendicular directions (the direction of arrow L and the direction of arrow R in FIG. 11) is performed (input) by a second bending operation knob 31C. The second bending operation knob 31C is provided at a position different from that of the first bending operation knob 19C in a state that the second bending operation knob 31C is not coaxial with the first bending operation knob 19C. The bending operation knobs 19C and 31C and members configured to transmit the bending operation take up more space in a grip section 3C. Thus, sufficient space is not secured inside a grip casing 17C. Moreover, the two bending operation knobs 19C and 31C that is rotatable relative to the grip casing 17C are attached to the grip casing 17C at different positions with respect to each other, so that it is difficult to keep the space between each of the bending operation knobs 19C and 31C and the grip casing 17C watertight. This facilitates the inflow of a liquid from the outside of the grip casing 17C into the inside of the grip casing 17C. Therefore, the washing of the grip section 3C after use is difficult.

In contrast, according to the present embodiment, the bending operation of the bending section 7 in the second perpendicular directions is performed (input) by the slide pad 31 which is the touched region detector. The slide pad 31 is shaped like a flat plate, and therefore takes up less space than the second bending operation knob 31C in the second comparative example. Members such as the electrical signal line 33, the motor 43, and the electrical signal line 45, which are configured to allow the second pulley 51 to be rotated by the bending operation in the slide pad 31, also take up little space. Accordingly, sufficient space is secured inside the grip casing 17. The slide pad 31 is fixed to the grip casing 17. It is thus easy to keep the space between the slide pad 31 and the grip casing 17 watertight. This efficiently prevents the inflow of a liquid from the outside of the grip casing 17 into the inside of the grip casing 17. Therefore, the grip section 3 is easily washed after use.

In the endoscope 1, the first perpendicular directions correspond to the up-and-down directions (UD directions) of the subject image obtained (captured) by the imaging element 11, and the second perpendicular directions correspond to the left-and-right directions (LR directions) of the subject image. Therefore, when the bending section 7 is bent in the up-and-down directions, force applied to the bending operation knob 19 by the surgeon is dynamically (mechanically) transmitted to the bending section 7. On the other hand, when the bending section 7 is bent in the left-and-right directions, the motor 42 is driven by an electrical signal generated by the bending operation in the slide pad 31, so that force applied to the slide pad 31 by the surgeon is not dynamically transmitted to the bending section 7. Actually, when the bending section 7 is bent, the bending section 7 is bent mainly in the up-and-down directions, and is hardly bent in the left-and-right directions. That is, in the bending operation in the up-and-down directions which is frequently performed, the force applied by the surgeon is dynamically transmitted to the bending section 7. Therefore, the surgeon can feel a proper sense of operation in the bending operation in the up-and-down directions. Consequently, the surgeon more easily performs (inputs) the bending operation of the bending section 7.

As the bending operation of the bending section 7 in the left-and-right directions is hardly performed, the force applied to the slide pad 31 by the surgeon does not need to be configured to be dynamically transmitted to the bending section 7. That is, even when the surgeon cannot feel a proper sense of operation in the bending operation in the left-and-right directions, there is no great effect on the bending operation of the bending section 7.

Thus, the endoscope 1 having the configuration described above has the following advantageous effects.

That is, in the endoscope 1, the bending operation knob 19 is attached to the first outer surface portion 21 in which the outer surface of the grip casing 17 faces toward one of the second perpendicular directions, and the touch surface 32 of the slide pad 31, which is the touched region detector, is located in the second outer surface portion 22 in which the outer surface of the grip casing 17 faces toward one of the first perpendicular directions. Therefore, when the surgeon grips the grip casing 17 with one of two hands, the bending operation knob 19 is easily rotated with the thumb F1, and the bending operation of the bending section 7 in the first perpendicular directions is easily performed (input). Moreover, the forefinger F2 or the middle finger F3 is easily moved on the touch surface 32 of the slide pad 31, and the bending operation of the bending section 7 in the second perpendicular directions is easily performed (input). Consequently, operability in the bending operation of the bending section 7 can be improved.

In the endoscope 1, the bending operation of the bending section 7 in the second perpendicular directions is performed by the slide pad 31 which is the touched region detector. The slide pad 31 is shaped like a flat plate, and therefore takes up little space. Members such as the electrical signal line 33, the motor 43, and the electrical signal line 45, which is configured to allow the second pulley 51 to be rotated by the bending operation in the slide pad 31, also take up little space. Accordingly, sufficient space can be secured inside the grip casing 17. The slide pad 31 is fixed to the grip casing 17. It is thus possible to easily keep the space between the slide pad 31 and the grip casing 17 watertight. This efficiently prevents the inflow of a liquid from the outside of the grip casing 17 into the inside of the grip casing 17. Therefore, the grip section 3 can be easily washed after use.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope comprising:
    an insertion section including a bending section which is configured to bend in first perpendicular directions perpendicular to longitudinal directions and in second perpendicular directions perpendicular to the longitudinal directions and perpendicular to the first perpendicular directions;
    a grip section which includes a grip casing, and which is provided to a proximal direction side of the insertion section;
    a bending operation knob which is attached to the grip casing, and which is configured to input a bending operation of the bending section in the first perpendicular directions;
    a touch surface which is exposed in an outer surface of the grip casing, and on which a bending operation of the bending section in the second perpendicular directions is input;
    a positional information calculator which is configured to calculate a positional information of a touched region with time, the touched region being a region that is touched in an input of the bending operation in the second perpendicular directions on the touch surface;
    a positional change detector which is configured to detect, in accordance with the positional information of the touched region with the time, a positional change of the touched region when the bending operation of the bending section in the second perpendicular directions is input;
    a drive member which is configured to be driven to bend the bending section in the second perpendicular directions; and
    a drive controller which is configured to control a drive state of the drive member in accordance with the positional change of the touched region.

2. The endoscope according to claim 1, wherein the grip casing includes a first outer surface portion in which the outer surface faces toward one of the second perpendicular directions and to which the bending operation knob is attached in a state that a rotation axis thereof is parallel to the second perpendicular directions, and a second outer surface portion in which the outer surface faces toward one of the first perpendicular directions and on which the touch surface is located.

3. The endoscope according to claim 2, wherein the positional change detector includes a displacement amount calculator which is configured to calculate a displacement amount of the touched region in the second perpendicular directions during the positional change of the touched region, and
    the drive controller is configured to control the drive state of the drive member in accordance with the displacement amount of the touched region in the second perpendicular directions.

4. The endoscope according to claim 1, wherein the positional change detector includes a displacement amount calculator which is configured to calculate a displacement amount of the touched region in reference directions parallel to the outer surface of the grip casing during the positional change of the touched region, and
    the drive controller is configured to control the drive state of the drive member in accordance with the displacement amount of the touched region in the reference directions.

5. The endoscope according to claim 4, wherein the reference directions are parallel to the second perpendicular directions.

6. The endoscope according to claim 1, further comprising an imaging element which is provided inside the insertion section, and which is configured to image a subject,
    wherein the first perpendicular directions correspond to up-and-down directions of a subject image obtained by the imaging element, and the second perpendicular directions correspond to left-and-right directions of the subject image.

7. The endoscope according to claim 1, wherein the positional information calculator is configured to calculate a position of a center of gravity of the touched region as the positional information of the touched region.

* * * * *